(12) United States Patent
Akatsuchi et al.

(10) Patent No.: US 11,486,885 B2
(45) Date of Patent: Nov. 1, 2022

(54) REAGENT FOR DETERMINATION OF COAGULATION TIME, PRODUCTION METHOD THEREFOR, REAGENT KIT, AND METHOD FOR DETERMINATION OF COAGULATION TIME

(71) Applicant: SYSMEX CORPORATION, Kobe (JP)

(72) Inventors: Kohei Akatsuchi, Kobe (JP); Takahiko Bandou, Kobe (JP); Naoki Yamamoto, Kobe (JP); Masako Aki, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 448 days.

(21) Appl. No.: 16/585,326

(22) Filed: Sep. 27, 2019

(65) Prior Publication Data
US 2020/0103421 A1    Apr. 2, 2020

(30) Foreign Application Priority Data
Sep. 28, 2018 (JP) .............................. JP2018-184895

(51) Int. Cl.
*G01N 33/86* (2006.01)
*C12Q 1/56* (2006.01)

(52) U.S. Cl.
CPC ............... *G01N 33/86* (2013.01); *C12Q 1/56* (2013.01); *G01N 2405/04* (2013.01)

(58) Field of Classification Search
None
See application file for complete search history.

(56) References Cited

U.S. PATENT DOCUMENTS

| | | | |
|---|---|---|---|
| 2017/0059594 A1 | 3/2017 | Yoshida et al. | |
| 2018/0031582 A1 | 2/2018 | Kumano et al. | |

FOREIGN PATENT DOCUMENTS

| | | |
|---|---|---|
| EP | 0 566 333 A1 | 10/1993 |
| EP | 2 339 021 A1 | 6/2011 |
| EP | 2 492 685 A1 | 8/2012 |
| EP | 2 790 024 A1 | 10/2014 |
| EP | 3 124 978 A1 | 2/2017 |
| EP | 3136 105 A1 | 3/2017 |
| JP | H07-270406 A | 10/1995 |
| JP | 2003-516525 A | 5/2003 |
| JP | 2012-181033 A | 9/2012 |
| JP | 2013-205087 A | 10/2013 |
| JP | 2014-190954 A | 10/2014 |
| JP | 2017-049040 A | 3/2017 |

OTHER PUBLICATIONS

Okuda, M., and Y. Yamamoto. "Usefulness of synthetic phospholipid in measurement of activated partial thromboplastin time: a new preparation procedure to reduce batch difference." Clinical & Laboratory Haematology 26.3 (2004): 215-223 (Year: 2004).*
Extended European Search Report dated Mar. 16, 2020 from the European Patent Office in application No. 19199997.8.
Kitchen, S., et al., "Lipid composition of seven APTT reagents in relation to heparin sensitivity", British Journal of Haematology, vol. 106, No. 3, 1999, pp. 801-808.
Fritsma, G., et al., "Recommendations for Appropriate Activated Partial Thromboplastin Time Reagent Selection and Utilization", Coagulation and Translation Medicine, American Journal of Clinical Pathology, vol. 137, No. 6, 2012, pp. 904-908.
Okuda et al., "Development of New APTT Reagent Based on Synthetic Phospholipids", Journal of the Japanese Society for Laboratory Hematology, vol. 3, No. 1.
Masahiro Okuda: "Usefulness of synthetic phospholipid in measurement of activated partial thromboplastin time (APTT)", Japanese Journal of Thrombosis and Hemostasis, 2005, vol. 16, No. 2, pp. 222-227.
Japanese Office Action dated May 10, 2022 in a counterpart Japanese patent application No. 2018-184895.

* cited by examiner

*Primary Examiner* — Robert J Yamasaki
(74) *Attorney, Agent, or Firm* — Sughrue Mion, PLLC (57) ABSTRACT

Disclosed is a reagent for determination of activated partial thromboplastin time, comprising: a phosphatidylcholine (PC); a phosphatidylserine (PS); and a phosphatidylethanolamine (PE), wherein a concentration ratio of the PS relative to the PC is not less than 0.16 and not more than 0.25, and a concentration of the PS is not less than 7 µg/mL and not more than 13 µg/mL.

6 Claims, 5 Drawing Sheets

REAGENT FOR DETERMINATION OF COAGULATION TIME, PRODUCTION METHOD THEREFOR, REAGENT KIT, AND METHOD FOR DETERMINATION OF COAGULATION TIME

CROSS REFERENCE TO RELATED APPLICATIONS

This application claims priority from prior Japanese Patent Application No. 2018-184895 filed on Sep. 28, 2018, entitled "REAGENT FOR DETERMINATION OF COAGULATION TIME, PRODUCTION METHOD THEREFOR, REAGENT KIT, AND METHOD FOR DETERMINATION OF COAGULATION TIME", the entire contents of which are incorporated herein by reference.

TECHNICAL FIELD

The present invention relates to a reagent for determination of activated partial thromboplastin time (APTT) and a method for producing the same. The present invention also relates to a reagent kit for determination of APTT. Furthermore, the present invention relates to a method for determination of APTT.

BACKGROUND

The APTT is a blood coagulation time, which reflects the function of intrinsic coagulation factors. The determination of APTT is used, for example, for screening tests for intrinsic coagulation factors, and monitoring of heparin therapy. In recent years, the determination of APTT has also been applied to screening tests for lupus anticoagulant (LA). LA is an antibody responsible for antiphospholipid antibody syndrome. LA inhibits the phospholipid required for blood coagulation, whereby the APTT becomes prolonged for LA-containing blood samples. Therefore, when blood samples are observed to have a prolonged in a screening test, these samples are suspected of having abnormalities of intrinsic coagulation factors or having autoantibodies such as LA.

In the determination of APTT, activators and phospholipids are used for the activation of intrinsic coagulation factors and the promotion of blood coagulation. The activators and phospholipids used are varied in type and composition, and various reagents for determination of APTT (also referred to hereinafter as "APTT reagents") are also commercially available. When commercially available APTT reagents are used for ATPP determination, normal blood samples have approximately similar coagulation times, which are around 30 seconds. However, it is known that these APTT reagents have great differences in the sensitivity to LA. For example, Masahiro Okuda et al., in Journal of the Japanese Society for Laboratory Hematology, Vol. 3, No. 1, pp. 124-131, 2002, described that the sensitivity to LA was examined using APTT reagents containing phosphatidylcholine (PC), phosphatidylserine (PS), and phosphatidylethanolamine (PE) as synthetic phospholipids, and ellagic acid as an activator. They described therein that the lower the concentration of the PS in the APTT reagent, the greater the Rosner Index becomes, which is an index of the sensitivity to LA.

SUMMARY OF THE INVENTION

The scope of the present invention is defined solely by the appended claims, and is not affected to any degree by the statements within this summary.

Among commercially available APTT reagents are those that are assessed to have high sensitivity to LA. Such reagents, however, also have a room for improvement in terms of the sensitivity to LA because some samples positive for LA have low LA concentrations. As an APTT reagent specialized for the detection of LA, there are known reagents containing phospholipids at low concentrations. These reagents, which have a low phospholipid concentration, make it easier that the reaction of inhibition of the phospholipids by LA occurs, resulting in an improvement in the sensitivity to LA. When these reagents are used for APTT determination, however, normal blood samples usually give prolonged coagulation times. Therefore, APTT reagents specialized for the detection of LA may not be suitable for screening tests for intrinsic coagulation factors. As mentioned above, APTT reagents are also used for monitoring of heparin therapy. In heparin therapy, the anticoagulant effect of heparin is monitored and the amount of heparin to be administered is adjusted, on the basis of APTT measurements. For this reason, APTT reagents having too high or too low sensitivity to heparin are not preferred. Therefore, there is a need to develop an APTT reagent that does not change the coagulation time for normal blood samples, has an improved sensitivity to LA, and has an appropriate sensitivity to heparin.

As described above, it has been described in Masahiro Okuda et al., Journal of the Japanese Society for Laboratory Hematology, Vol. 3, No. 1, pp. 124-131, 2002, that the concentration of the PS in the APTT reagent affects the sensitivity to LA. However, as results from examinations of the composition of the phospholipids in APTT reagents, the present inventors have found that the sensitivity to LA is affected not only by the concentration of the PS, but also by the ratio of the concentration of the PS relative to that of the PC. In addition, APTT reagents having the phospholipid composition that was found by the present inventors did not result in a variation in the coagulation times of normal plasmas and had an appropriate sensitivity to heparin. From these findings, the present inventors have completed the present invention.

A first aspect of the present invention provides a reagent for determination of APTT, including a PC, a PS, and a PE, in which the reagent has a concentration ratio of the PS relative to the PC that is not less than 0.16 and not more than 0.25, and a concentration of the PS that is not less than 7 μg/mL and not more than 13 μg/mL.

A second aspect of the present invention provides a reagent kit for determination of APTT, including a first reagent containing a PC, a PS, and a PE, and a second reagent containing calcium ions, in which the first reagent has a concentration ratio of the PS relative to the PC that is not less than 0.16 and not more than 0.25, and a concentration of the PS that is not less than 7 μg/mL and not more than 13 μg/mL.

A third aspect of the present invention provides a method for determination of APTT, including mixing a blood sample, a first reagent containing a PC, a PS, and a PE, and a second reagent containing calcium ions, and measuring a coagulation time of the blood sample, in which the first reagent has a concentration ratio of the PS relative to the PC that is not less than 0.16 and not more than 0.25, and a concentration of the PS that is not less than 7 μg/mL and not more than 13 μg/mL.

A fourth aspect of the present invention provides a method for producing a reagent for determination of APTT, including mixing a PC, a PS, and a PE, in which the reagent has a concentration ratio of the PS relative to the PC that is not less than 0.16 and not more than 0.25, and a concentration of the PS that is not less than 7 μg/mL and not more than 13 μg/mL.

DETAILED DESCRIPTION OF THE PREFERRED EMBODIMENTS

1. Reagents for Determination of Activated Partial Thromboplastin Time

An APTT reagent according to an embodiment comprises a phosphatidylcholine (PC), a phosphatidylserine (PS), and a phosphatidylethanolamine (PE) as phospholipids. The phospholipids that are contained in the APTT reagent can be naturally occurring phospholipid, or alternatively synthetic phospholipids. Examples of naturally occurring phospholipids include phospholipids derived from, for example, rabbit brain, bovine brain, human placenta, soybean, egg yolk, and others. The phospholipids preferably are synthetic phospholipids, or naturally derived phospholipids purified to a purity of 99% or more, from the viewpoint of improving the sensitivity to LA. The phospholipids can be provided in solid form or in a solution in which they are dissolved in an organic solvent such as chloroform.

In the PC, the PS, and the PE, their fatty acid side chains (acyl groups) are not particularly limited, and are, for example, acyl groups having 8 to 20 carbon atoms, preferably 14 to 18 carbon atoms. Such acyl groups include, for example, a lauroyl group, myristoyl group, palmitoyl group, a stearoyl group, an oleoyl group, and the like. Each of the PC, the PS, and the PE has two fatty acid side chains within the molecule. The two fatty acid side chains in each of the PC, the PS, and the PE molecules may be the same or different.

Specific examples of the PC include dilauroylphosphatidylcholine, dimyristoylphosphatidylcholine, dipalmitoylphosphatidylcholine, distearoylphosphatidylcholine, dioleoylphosphatidylcholine, and others. Specific examples of the PS include dilauroylphosphatidylserine, dimyristoylphosphatidylserine, dipalmitoylphosphatidylserine, distearoylphosphatidylserine, dioleoylphosphatidylserine, and others. Specific examples of the PE include dilauroylphosphatidylethanolamine, dimyristoylphosphatidylethanolamine, dipalmitoylphosphatidylethanolamine, distearoylphosphatidylethanolamine, dioleoylphosphatidylethanolamine, and others.

In the embodiment, the phospholipids in the APTT reagent preferably are in the form of liposomes. The average particle size of liposomes is not particularly limited, and is, for example, not more than 1000 nm, preferably not less than 100 nm and not more than 800 nm. As used herein, the term "average particle size of liposomes" refers to a Z-average particle diameter, based on the cumulant method, obtained by measuring the diameters of liposomes in a dispersion of the liposomes at 25° C. using a particle size analyzer "Zetasizer Nano ZSP" (Spectris Co., Ltd.) on a particle-size analysis mode, in which a dynamic light scattering method is employed as the principle of measurement. TAPS buffer is used as a dispersion medium for the liposome dispersion. The analyzer device is equipped with a data analysis software, which automatically analyzes the measurement data to calculate the Z-average particle diameter.

In the embodiment, the APTT reagent is characterized by having a concentration ratio of the PS relative to the PC (also referred to hereinafter as a "PS/PC ratio") that is not less than 0.16 and not more than 0.25. The PS/PC ratio is calculated by dividing the value of the concentration of the PS in the APTT reagent by that of the PC in the reagent. The lower limit of the PS/PC ratio can be selected from, for example, 0.16, 0.17, 0.18, 0.19, 0.20, 0.21, 0.22, 0.23, and 0.24. The upper limit of the PS/PC ratio is preferably 0.25 in terms of the sensitivity to LA and to heparin. The upper limit of the PS/PC ratio can be selected from, for example, 0.25, 0.24, 0.23, 0.22, 0.21, 0.20, 0.19, 0.18, and 0.17. Numerical ranges of the PS/PC ratio can be determined as appropriate by combining the above-described values of the upper limit and of the lower limit. In addition to the range of not less than 0.16 and not more than 0.25, the numerical range of the PS/PC ratio includes, for example, ones of not less than 0.16 and not more than 0.24, not less than 0.17 and not more than 0.25, and not less than 0.17 and not more than 0.24, to which the present disclosure is not limited.

The respective concentrations of the PC, the PS, and the PE in the APTT reagent can be calculated by dividing the respective weights of the PC, the PS, and the PE used in the preparation of the APTT reagent by the volume of a liquid added for the preparation thereof. The PC, the PS, and the PE each preferably have a purity of 99% or more. As a specific example, the APTT reagent is prepared as follows. 50 mg, 10 mg, and 15 mg of a PC, a PS, and a PE in solid form, respectively, are weighed and dissolved in chloroform. The chloroform is evaporated from the resulting chloroform solution of the phospholipids, by an evaporator, to obtain a thin film of the phospholipids. A buffer solution (100 mL) is added to the phospholipid thin film to swell it to prepare a liposome-containing buffer solution. The whole volume of the liposome-containing buffer solution is mixed with a solution of an activator (900 mL) to prepare an APTT reagent. In this case, the concentrations of the PC, the PS, and the PE in the resultant APTT reagent are 50 μg/mL (50 mg/1000 mL), 10 μg/mL (10 mg / 1000 mL), and 15 μg/mL (15 mg/1000 mL), respectively. The present disclosure is not limited to this example.

The APTT reagent according to the embodiment is characterized by having a concentration of the PS that is not less than 7 μg/mL and not more than 13 μg/mL, in terms of the sensitivity to LA and to heparin. The lower limit of the concentration of the PS can be selected from, for example, 7, 8, 9, 10, 11 and 12 µg/mL. The upper limit of the concentration of the PS can be selected from, for example, 13, 12, 11, 10, 9 and 8 µg/mL. Numerical ranges of the concentration of the PS can be determined as appropriate by combining the above-described values of the upper limit and of the lower limit. In addition to the range of not less than 7 µg/mL and not more than 13 µg/mL, the numerical range of the concentration of the PS includes, for example, ones of not less than 7 µg/mL and not more than 12 µg/mL, and not less than 8 µg/mL and not more than 13 µg/mL, to which the present disclosure is not limited.

The concentration of the PC in the APTT reagent is not particularly limited, as long as the reagent has a PS/PC ratio and a concentration of the PS of which each is within the numerical range described above. Thus, the concentration of the PC in the APTT reagent can be determined from the PS/PC ratio and the concentration of the PS. For example, when the PS/PC ratio is 0.25 and the concentration of the PS is 7 µg/mL, the concentration of the PC will be 28 µg/mL. In the embodiment, the upper limit of the concentration of the PC in the APTT reagent may be, for example, less than 50 µg/mL. In this case, the upper limit of the concentration of the PC in the APTT reagent can be selected from, for example, 49, 48, 47, 46, and 45 µg/mL. The lower limit of the concentration of the PC in the APTT reagent can be selected from, for example, 28, 29, 30, 31, 32, 33, 34, 35, 36, 37, 38, 39, 40, 41, 42, 43, and 44 µg/mL. Numerical ranges of the concentration of the PC can be determined as appropriate by combining the above-described values of the upper limit and of the lower limit. The numerical range of the concentration of the PC in the APTT reagent includes, for example, ones of not less than 28 µg/mL and less than 50 µg/mL, not less than 28 µg/mL and not more than 49 µg/mL, not less than 30 µg/mL and less than 50 µg/mL, and not less than 30 µg/mL and not more than 49 µg/mL, to which the present disclosure is not limited.

Alternatively, the upper limit of the concentration of the PC in the APTT reagent may be 60 µg/mL. In this case, the lower limit of the concentration of the PC in the APTT reagent is preferably higher than 50 µg/mL, and can be selected from, for example, 51, 52, 53, 54, and 55 µg/mL. Numerical ranges of the concentration of the PC can be determined as appropriate by combining these values of the upper limit and of the lower limit. The numerical range of the concentration of the PC in the APTT reagent includes, for example, ones of more than 50 µg/mL and not more than 60 µg/mL, and not less than 51 µg/mL and not more than 60 µg/mL, to which the present disclosure is not limited.

The concentration of the PE in the APTT reagent is not particularly limited. The lower limit of the concentration of the PE in the APTT reagent is preferably more than 9 µg/mL, and can be selected from, for example, 10, 11, 12, 13, 14, 15, 16, 17, 18, and 19 µg/mL. The upper limit of the concentration of the PE in the APTT reagent is preferably less than 25 µg/mL, and can be selected from, for example, 24, 23, 22, 21, and 20 µg/mL. Numerical ranges of the concentration of the PE can be determined as appropriate by combining these values of the upper limit and of the lower limit. Numerical ranges of the concentration of the PE in the APTT reagent are, for example, ranges of more than 9 µg/mL and less than 25 µg/mL, not less than 10 µg/mL and less than 25 µg/mL, and not less than 10 µg/mL and not more than 20 µg/mL, to which the present disclosure is not limited.

The solvent that is used in an APTT reagent according to the embodiment can be selected as appropriate from aqueous solvents usually used in the field of blood testing. Such aqueous solvents include, for example, water, saline, buffers, and others. The buffers have a pH of preferably not less than 6 and not more than 8, more preferably not less than 7 and not more than 7.6. Examples of the buffers include Good's buffers such as HEPES, TAPS, MOPS, BES, and TES, Tris-hydrochloric acid buffer (Tris-HCl), Owren's Veronal buffer, imidazole-hydrochloric acid buffer, and others. If necessary, glycine may be added to these buffers.

The APTT reagent according to the embodiment is usually has a pH of not less than 6 and not more than 8, preferably not less than 7 and not more than 7.6. The pH of the APTT reagent can be adjusted by addition of any of the above-described buffers.

The APTT reagent according to the embodiment preferably contains an activator. The activator can be any substance that activates contact factors in the intrinsic coagulation pathway. Such substances include, for example, ellagic acid compounds, silica, kaolin, celite, and others. The ellagic acid compound can be any of ellagic acid, a salt thereof, and a metal complex thereof. One of these activators may be used, or two or more may be used in combination. In the embodiment, the ATPP reagent particularly preferably employs an ellagic acid compound as the activator. The ellagic acid compound is particularly preferably a metal complex of ellagic acid containing a metal ion, such as zinc ion, manganese ion, and aluminum ion.

For example, when an ellagic acid compound is used as the activator, the concentration thereof in the APTT reagent usually is not less than 10 µM and not more than 400 µM, preferably not less than 30 µM and not more than 150 µM. When silica is used as the activator, the concentration thereof in the APTT reagent usually is not less than 0.1 mg/mL and not more than 1.0 mg/mL, preferably not less than 0.2 mg/mL and not more than 0.6 mg/mL.

In the embodiment, the APTT reagent preferably contains a metal ion-forming compound for the sake of activating contact factors and suppressing the generation of precipitates. The metal ion-forming compound is not particularly limited, as long as metal ions are generated from the compound in the APTT reagent and the anion resulting from the compound causes no inhibition of blood coagulation reaction. Examples of the metal ion-forming compound can be, for example, salts of metals and organic or inorganic acids. Among these, preference is given to salts of metals and inorganic acids, and such salts include, for example, salts of metals and acids such as hydrochloric acid, sulfuric acid, and nitric acid. More preferable metal salts are salts of at least one metal selected from zinc, manganese, aluminum, and nickel, and examples of these salts include zinc chloride, manganese chloride, aluminum chloride, nickel chloride, and others. The metal ion-forming compound can be an anhydride or a hydrate. One of the metal ion-forming compounds may be used, or two or more may be used in combination. The concentration of the metal ion-forming compound in the APTT reagent is, for example, not less than 1 µM and not more than 1 mM, preferably not less than 10 µM and not more than 500 µM.

When the APTT reagent contains an ellagic acid compound, the APTT reagent preferably contains an aromatic-ring-containing amino acid for the sake of preventing the precipitation of the ellagic acid compound. The term "aromatic-ring-containing amino acid" refers to an amino acid having, in the side chain thereof, at least one ring belonging to an aromatic group. Such an aromatic ring includes, for example, a benzene ring, a fused benzene ring, a non-benzene aromatic ring, and a heteroaromatic ring. The aromatic-ring-containing amino acid has one or more aromatic rings. When the aromatic-ring-containing amino acid has a plurality of aromatic rings, the aromatic rings may be the same or different from each other.

The aromatic-ring-containing amino acid preferably is an a-amino acid, more preferably any of amino acids of the types found in proteins and derivatives thereof. These amino acids include phenylalanine, tyrosine, tryptophan, histidine, and derivatives thereof. Here, the term "derivative" refers to a compound in which any of the hydrogen atoms or hydroxyl group on the aromatic ring contained in the above-mentioned amino acid is substituted with a suitable substituent. Such a substituent is not particularly limited, as long as the substitution therewith does not disturb the blood coagulation reaction, and the solubilization or dispersion of the ellagic acid. In a preferred embodiment, the aromatic-ring-containing amino acid includes phenylalanine and tyrosine. Among these, phenylalanine is particularly preferred. The aromatic-ring-containing amino acid can be any of L-form, D-form, and a mixture thereof. The aromatic-ring-containing amino acid can be a naturally occurring amino acid or a synthetic amino acid.

In the embodiment, the APTT reagent may further contain an additive for improving the shelf life and stability. Such an additive includes, for example, preservatives, antioxidants, stabilizers, and others. The preservatives include, for example, antibiotics such as aminoglycoside antibiotics, sodium azide, and others. The antioxidants include, for example, butylated hydroxyanisole, and others. The stabilizers include, for example, polyethylene glycol, polyvinyl pyrrolidone, and others.

The APTT reagent according to the embodiment can be used under general conditions for APTT determination, as in cases where conventional APTT reagents are used. The APTT reagent according to the embodiment can be employed in screening tests for intrinsic coagulation factors, monitoring of heparin therapy, and LA screening tests, as in cases where conventional APTT reagents are used. The APTT reagent according to the embodiment can be mixed with a blood sample at a mixing ratio of approximately 8:2 to 2:8, preferably 5:5, by volume. In other words, the amount of the APTT reagent according to the embodiment to be added can be an amount (volume) that is not less than 0.25 times and not more than 4 times relative to that of a blood sample. Preferably, the amount of the APTT reagent according to the embodiment to be added is equal to the amount (volume) of a blood sample.

The APTT reagent according to the embodiment has improved sensitivity to LA, relative to conventional APTT reagents. The sensitivity to LA can be evaluated using, for example, the ratio of the coagulation time of an LA-containing sample to that of a normal sample (which also referred to hereinafter as an "LA ratio") as an index. The normal sample preferably is a plasma pool prepared from plasmas obtained from healthy persons, or a commercially available normal plasma. The LA-containing sample preferably is plasma obtained from an LA-positive patient, or commercially available LA-containing plasma. The LA ratio desirably is, for example, 1.77 or more when the APTTs of an LA-containing sample and a normal sample are determined with appropriate use of the APTT reagent together with an aqueous solution containing calcium ions.

When used to determine the coagulation times of normal samples, the APTT reagent according to the embodiment can give measurement results similar to those obtained by conventional APTT reagents. For example, it is desirable that a given normal plasma (for example, Coagtrol IX, manufactured by Sysmex Corporation) has an APTT of about 30 seconds (for example, not less than 25 seconds and not more than 35 seconds) when subjected to APTT determination with appropriate use of the APTT reagent together with an aqueous solution containing calcium ions. Also, it is desirable that a given abnormal plasma (for example, Coagtrol IIX, manufactured by Sysmex Corporation) has an APTT within the range of 60 to 100 seconds when subjected to APTT determination.

In heparin therapy, the anticoagulant effect of heparin is monitored and the amount of heparin to be administered is adjusted, on the basis of APTT measurements. For this reason, APTT reagents having too high or too low sensitivity to heparin are not preferred. The APTT reagent according to the embodiment has an appropriate sensitivity to heparin. The sensitivity to heparin can be evaluated using, for example, the ratio of the coagulation time of a heparin-containing sample to that of a normal sample (which also referred to hereinafter as a "heparin ratio") as an index. The heparin-containing sample preferably is plasma obtained from a patient who has been administered with heparin, or commercially available heparin-containing plasma. The heparin ratio desirably is, for example, not less than 2.19 and not more than 2.86 when the APTTs for a heparin-containing sample and a normal sample are determined with appropriate use of the APTT reagent together with an aqueous solution containing calcium ions.

Figure 1:
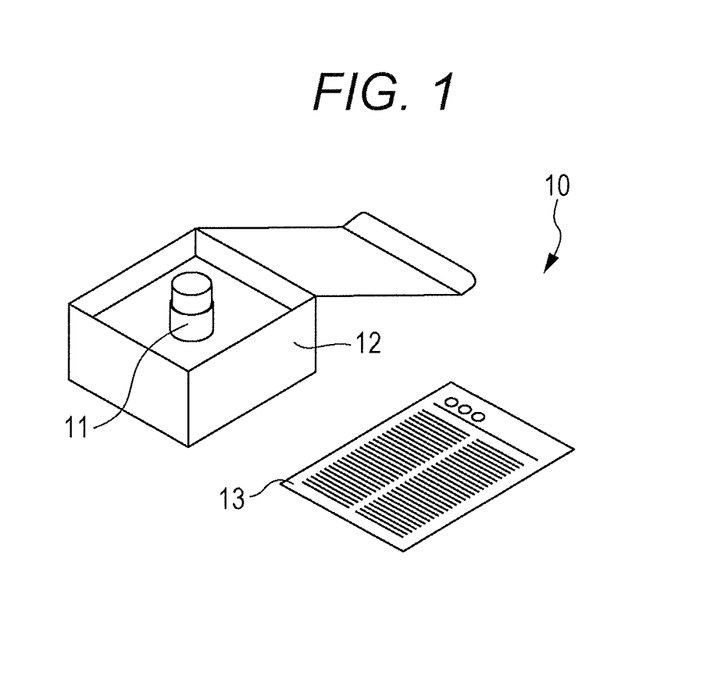
FIG. 1 is a schematic view showing an example of an APTT reagent according to an embodiment.

In the embodiment, the APTT reagent is placed into a container, which in turn may be packaged in a box to be provided for users. The box may be supplied with a package insert describing how to use the APTT reagent. FIG. 1 shows an example of the APTT reagent according to the embodiment. Referring to FIG. 1, 10 indicates the APTT reagent; 11 indicates a first container containing the APTT reagent; 12 indicates a packaging box; and 13 indicates a package insert.

2. Methods for Producing Reagents for Determination of Activated Partial Thromboplastin Time In the embodiment, a method for producing a reagent for determination of APTT (also referred to hereinafter simply as a "production method") comprises mixing a PC, a PS, and a PE so that the APTT reagent produced has a concentration ratio of the PS relative to the PC that is not less than 0.16 and not more than 0.25 and a concentration of the PS that is not less than 7 µg/mL and not more than 13 µg/mL. The APTT reagent according to the embodiment can be produced by the production method according to the embodiment. The details of the PC, the PS and the PE are as described above.

In the embodiment, the PC, the PS, and the PE are preferably mixed so as to form liposomes of the phospholipids. The mixing of the PC, the PS and the PE and the formation of liposomes are carried out, for example, in the following way. Respective predetermined amounts of a PC, a PS, and a PE in solid are weighed and dissolved in an organic solvent. The organic solvent preferably is one that can dissolve the phospholipids and has a low boiling point. Such organic solvents include, for example, chloroform, methanol, and mixtures thereof. Each of the PC, the PS and the PE is also commercially available in solutions in which it has previously been dissolved in an organic solvent. In the embodiment, the respective solutions of the PC, the PS, and the PE may be mixed. The organic solvent is evaporated from the resulting solution of the phospholipids, for example, by an evaporator, to obtain thin film of the phospholipids. To this thin film is added a suitable aqueous solvent (preferably a buffer). The thin film is allowed to be swelled by the aqueous solvent, thereby to generate a liquid containing liposomes. Thus, the APTT reagent according to the embodiment that contains the PC, the PS and the PE as phospholipids can be produced. Details of the aqueous solvent and buffer are as described above.

For the production method, the weights of a PC and a PS and the amount of an aqueous solvent to be used are decided as appropriate, so that the resulting APTT reagent has a concentration ratio of the PS to the PC that is not less than 0.16 and not more than 0.25 and a concentration of the PS that is not less than 7 µg/mL and not more than 13 µg/mL. When a solution containing an activator described below is to be added to the APTT reagent, the weights of a PC and a PS and the amount of an aqueous solvent to be used are decided taking into account the amount of the solution to be added. The respective concentrations of the PC, the PS and the PE in the APTT reagent are calculated using the procedures detailed above.

In the embodiment, the resulting solution is preferably stirred after the aqueous solvent is added to the thin film of the phospholipids, in order that it is allowed to be sufficiently swelled. The stirring is performed using, for example, a stirrer. The stirring speed is not particularly limited, as long as the liposomes are intact during the stirring, and can be, for example, not less than 400 rpm and not more than 650 rpm. The stirring time is usually not less than 45 minutes and not more than 120 minutes, preferably not less than 60 minutes and not more than 90 minutes.

In the embodiment, the liposome-containing solution is preferably sonicated in order to disperse the liposomes therein. The sonication can be done at a frequency of, for example, not less than 35 kHz and not more than 40 kHz. The sonication can be done for a duration of not less than 5 minutes and not more than 20 minutes.

In the embodiment, the liposome-containing solution after the sonication may be subjected to an extruder treatment using a membrane filter having a desired pore size and an extruder, in order to make the liposome particle sizes homogeneous. As used herein, the term "liposome particle size" refers to a value obtained by measuring the diameters of liposomes in a dispersion of the liposomes at 25° C. using a particle size analyzer "Zetasizer Nano ZSP" (Spectris Co., Ltd.) on a particle-size analysis mode. TAPS buffer is used as a dispersion medium for the liposome dispersion. The extruder treatment, whereby the average liposome particle size is reduced, is expected to have an effect of preventing the prolongation of normal coagulation time to 30 seconds or longer.

The production method for the ATPP reagent according to the embodiment preferably comprises mixing a mixture of a PC, a PS, and a PE (or a liposome-containing liquid as described above) and a solution containing an activator. In this case, the APTT reagent according to the embodiment that contains the PC, the PS, and the PE as phospholipids and the activator can be produced. The details of the activator are as described above. The solution containing the activator can be prepared by dissolving or dispersing the activator in a suitable aqueous solvent. When ellagic acid or salt thereof is used as the activator, a metal ion-forming compound may be added to a solution containing ellagic acid or salt thereof. Thus, a solution containing the metal complex of ellagic acid can be prepared. The details of the metal ion-forming compound are as described above.

If necessary, the APTT reagent may be further mixed with at least one of a metal ion-forming compound, an aromatic-ring-containing amino acid, and an additive. Details of the aromatic-ring-containing amino acid and the additive are as described above.

3. Reagent Kits for Determination of Activated Partial Thromboplastin Time

A reagent kit for determination of APTT according to the embodiment (also referred to hereinafter as an "APTT reagent kit") comprises a first reagent containing a PC, a PS, and a PE as phospholipids, and a second reagent containing calcium ions. The APTT reagent kit is characterized in that the first reagent has a PS/PC ratio of not less than 0.16 and not more than 0.25 and a concentration of the PS of not less than 7 µg/mL and not more than 13 µg/mL. As the first reagent, the APTT reagent according to the embodiment described above can be used. The details of the first reagent are the same as those described for the APTT reagent according to the embodiment.

The second reagent is a reagent which is added to a mixture of a blood sample and the first reagent, thereby to initiate blood coagulation. In the embodiment, the second reagent preferably is an aqueous solution containing calcium ions. The aqueous solution containing calcium ions is preferably an aqueous solution of a calcium salt. The calcium salt includes, for example, calcium chloride, and the like. The concentration of calcium ions in the second reagent is usually not less than 2.5 mM and not more than 40 mM, preferably not less than 10 mM and not more than 30 mM. When an easily water-soluble calcium salt such as calcium chloride is used, the concentration of calcium ions in the second reagent may be expressed in terms of the concentration of the calcium salt.

Figure 2:
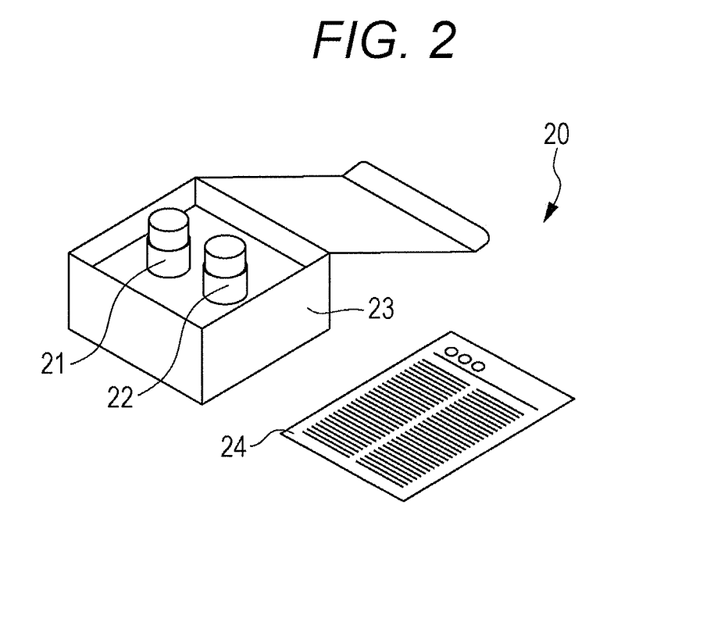
FIG. 2 is a schematic view showing an example of an APTT reagent kit according to the embodiment.

In the embodiment, the first reagent is placed into a first container and the second reagent is placed into a second container, and the two containers in turn may be packaged in a box to be provided for users. The box may be supplied with a package insert describing how to use the APTT reagent kit. FIG. 2 shows an example of the APTT reagent kit according to the embodiment. Referring to FIG. 2, 20 indicates the APTT reagent kit; 21 indicates a first container containing the first reagent; 22 indicates a second container containing the second reagent; 23 indicates a packaging box; and 24 indicates a package insert.

The APTT reagent kit according to the embodiment is provided with, for example, an aqueous dilution medium, a reference plasma, and the like. The aqueous dilution medium is an aqueous medium for diluting the first reagent. For example, when LA is detected using the APTT reagent kit, the first reagent is diluted with the aqueous dilution medium, thereby reducing the concentration of the phospholipids in the first reagent. As a result, the reaction of inhibition of the phospholipids by LA becomes easier to occur. The APTT determined using the first reagent that has been diluted and the second reagents is called "diluted APTT" (dAPTT) in the field of blood testing. The reference plasma include, for example, normal plasma, plasma for accuracy control, plasma lacking various coagulation factors, LA-containing plasma, heparin-containing plasma, and the like.

4. Methods for Determination of Activated Partial Thromboplastin Time

In the embodiment, a method for determination of APTT (also referred to hereinafter as an "APTT determination method") comprises mixing a blood sample, a first reagent containing a PC, a PS, and a PE as phospholipids, and a second reagent containing calcium ions, and determining the coagulation time of the mixture. The APTT determination method is characterized in that the first reagent has a PS/PC ratio of not less than 0.16 and not more than 0.25 and a concentration of the PS of not less than 7 µg/mL and not more than 13 µg/mL. As the first reagent, the APTT reagent according to the embodiment described above can be used. Alternatively, the first and the second reagents can be replaced with those contained in an APTT reagent kit according to the embodiments.

As the blood sample, use is made of blood taken from a subject or plasma prepared therefrom. Preferably, the blood sample is plasma. The blood sample may contain a known anticoagulant commonly used for blood testing that has been added thereto. Such an anticoagulant includes, for example, trisodium citrate. In cases where the APTT determination method according to the embodiment is used for monitoring of heparin therapy, blood or plasma from a subject to which heparin has been administered is used. The blood sample may be incubated, for example, at a temperature of not less than 35° C. and not more than 40° C. for a period of time of not less than 30 seconds and not more than 2 minutes, before the addition of the first reagent.

In the embodiment, first, a blood sample is mixed with the first reagent. The first reagent can be mixed with the blood sample at a mixing ratio of approximately 8:2 to 2:8, preferably 5:5, by volume. In other words, the amount of the first reagent to be added can be an amount (volume) that is not less than 0.25 times and not more than 4 times relative to the amount (volume) of the blood sample. Preferably, the amount of the first reagent to be added is equal to the amount (volume) of the blood sample. After the blood sample is mixed with the first reagent, the mixture is preferably incubated under predetermined conditions. The predetermined conditions include, for example, conditions where incubation is carried out at a temperature of not less than 35° C. and not more than 40° C. for a period of time of not less than 2 minutes and not more than 5 minutes.

Subsequently, the mixture of the blood sample and the first reagent is mixed with the second reagent. Hereinafter, the mixture of the blood sample, the first reagent, and the second reagent is also referred to as a "measurement sample." The amount of the second reagent to be added can be an amount (volume) resulting in a concentration of calcium ions in the measurement sample that is usually not less than 2 mM and not more than 20 mM, preferably not less than 4 mM and not more than 10 mM. The preparation of the measurement sample can be performed by manual procedures or with a fully automated analyzer. Such an analyzer is, for example, a CS series analyzer for fully automated blood coagulation measurement (Sysmex Corporation).

In the embodiment, the APTT determination method measures the time to coagulation from the time at which the second reagent is added to the measurement sample. The coagulation time may be determined by manual procedures or with a fully automated analyzer. In manual procedures, a stopwatch or the like is used to visually measure the time to precipitation of fibrin. In cases of using a fully automated analyzer, the coagulation time can be determined in method for optical or physical measurements. In optical measurement methods, for example, the measurement sample is irradiated with light, thereby to obtain optical information, on such as transmittance, absorbance, and scattered light intensity, to determine its coagulation time based thereon. In physical measurement methods, for example, a steel ball is used to obtain physical information, on such as the viscosity of the measurement sample, to determine its coagulation time based thereon. The fully automated analyzer to be used is not particularly limited. For example, with a CS series analyzer for fully automated blood coagulation measurement (Sysmex Corporation), the coagulation time for samples can be determined based on optical information such as transmittance, absorbance, and scattered light intensity. Alternatively, with STA Compact (Roche Diagnostics K.K.), another fully automated analyze for blood coagulation and fibrinolysis measurement, the coagulation time for samples can be determined based on physical information such as viscosity.

In the APTT determination method according to the embodiment, the presence or absence of LA in a blood sample can be determined if it is observed to have a prolonged coagulation time. Whether or not blood samples have a prolonged coagulation time is preferably determined based on the result of comparison of the coagulation times of the blood samples to that of a normal sample. An example of this determination is described as follows. The normal sample uses a plasma pool prepared from plasmas obtained from healthy persons, or a commercially available normal plasma, such as Coagtrol N (Sysmex Corporation). The coagulation time of the normal sample is determined using the first and the second reagents as in the blood sample. When the blood sample has a coagulation time longer than that of the normal sample, the coagulation time of the blood sample is determined to be prolonged.

In a preferred embodiment, the coagulation time of the blood sample is divided by that of the normal sample, thereby to obtain the ratio of the coagulation time of the blood sample relative to that of the normal sample (also referred to hereinafter as an "APTT ratio"). If the APTT ratio is equal to or more than a predetermined threshold value, then the blood sample is determined to have a prolonged coagulation time. The predetermined threshold value of the APTT ratio can be defined by accumulation of APTT data for healthy people and patients with various diseases who are observed to have prolonged APTTs. The predetermined threshold value of the APTT ratio can be determined from, for example, a range of not less than 1.2 and not more than 1.5.

In the embodiment, whether or not the blood sample contains LA is preferably determined by a mixing test. Such a mixing test itself is known in the art. An example of this determination is described as follows. A mixed sample is prepared from a blood sample and an above-mentioned normal sample. The mixing ratio of the blood sample to the normal sample can be determined as appropriate, depending on the amount of the blood sample, the type of the quantification index as described below, and others. The percentage of the blood samples in the mixed sample is selected from, for example, 5, 10, 15, 20, 25, 30, 35, 40, 45, 50, 55, 60, 65, 70, 75, 80, 85, 90, and 95% (v/v). It is preferable to prepare a mixed sample in which the blood sample is mixed at a percentage of 50% (v/v), among these percentages. The number of mixed samples may be one or more.

The coagulation time of the mixed sample, as well as those of the blood sample and the normal sample, is determined using the first and the second reagents. Whether or not the blood sample contains LA is then determined based on the coagulation times of the mixed sample, of the blood sample, and of the normal sample. For example, if the coagulation time of the mixed sample is comparable to that of the blood sample, then it is possible that the blood sample is determined to be suspected of containing LA. On the other hand, if the coagulation time of the mixed sample is comparable to that of the normal sample, then it is possible that the blood sample is determined not to contain LA. In this case, the blood sample is suspected of lacking a coagulation factor(s).

In a preferred embodiment, the coagulation times of the blood sample, the normal sample, and the mixed sample are used to obtain a quantification index, and based on the value of which a determination is made as to whether or not the blood sample contains LA. For example, if the quantification index value is greater than a predetermined threshold value, then it is possible that the blood sample is determined to be suspected of containing LA. On the other hand, if the quantification index value is not less than a predetermined threshold value, then it is possible that the blood sample is determined not to contain LA.

The quantification index is not particularly limited, as long as it is for evaluating quantitatively the results of a cross-mixing test based on the coagulation times of the blood sample, the normal sample, and the mixed sample. Known quantification indices can be used. Known quantification indices include, for example, Index of Circulating Anticoagulant (ICA), Percent Correction (PC), and Response Curve-Score (RC-S). Among these, ICA is particularly preferable. ICA is disclosed in Pengo V. et al., Update of the guidelines for lupus anticoagulant detection. Journal of Thrombosis and Haemostasis 2009; 7:1737-1740. PC is disclosed in Chang S-H. et al., "Percent Correction" Formula for Evaluation of Mixing Studies., Am J Clin Pathol 2002; 117:62-73. RC-S is disclosed in NAITO, Sumiyoshi, et al., Evaluation and usefulness of LA detection by new determination method of cross-mixing test, *Rinsho-Byori* [The official journal of Japanese Society of Laboratory Medicine] (in Japanese), vol. 60, Suppl., 166, 2012.

ICA, which is also called Rosner Index, is an index used for the determination of LA-positive samples. ICA is calculated by the following equation.

$$ICA=[(D-A)/G]\times 100$$

wherein A is a coagulation time of a normal sample; D is a coagulation time of a mixed sample of the normal sample and a blood sample at a percentage of 50% (v/v); and G is a coagulation time of the blood sample.

Each of PCs is calculated using the calculation formula corresponding to the percentage of the blood sample in a mixed sample, as described below.

$$PC(9:1)=[(G-B)/(G-A)]\times 100$$

$$PC(8:2)=[(G-C)/(G-A)]\times 100$$

$$PC(5:5)=[(G-D)/(G-A)]\times 100$$

$$PC(2:8)=[(G-E)/(G-A)]\times 100$$

$$PC(1:9)=[(G-F)/(G-A)]\times 100$$

wherein A is a coagulation time of a normal sample; B, C, D, E, and F are a coagulation time of a mixed sample in which the normal sample is mixed a blood sample of which the percentage is 10% (v/v), 20% (v/v), 50% (v/v), 80% (v/v), and 90% (v/v), respectively; G is a coagulation time of the blood sample.

RC-S, which is an index to which the Rosner index is applied, is calculated as follows. First, scores for mixed samples in which a normal sample is mixed with a blood sample of which the percentages is 20 and 50% (v/v) are calculated according to the following equations.

$$RC-S(20)=[(C-B)/D]\times 100$$

$$RC-S(50)=[(D-C)/E]\times 100$$

wherein B, C, D, and E are a coagulation time of a mixed sample in which a normal sample is mixed with a blood sample of which the percentage is 10% (v/v), 20% (v/v), 50% (v/v), and 80% (v/v), respectively.

Next, assuming the linearity of the response curve of the cross mixing test, control scores for the mixed samples in which the ratio of the blood sample is 20 and 50% (v/v) are calculated, according to the following equations.

$$RC-Sc(20)=[[(3\times B+D)/4-B]/D]\times 100$$

$$RC-Sc(50)=[[(C+E)/2-B]/E]\times 100$$

wherein B, C, D, and E are a coagulation time of a mixed sample in which a normal sample is mixed with a blood sample of which the percentage is 10% (v/v), 20% (v/v), 50% (v/v), and 80% (v/v), respectively.

Then, the ratio of the score (S) to the control score (Sc) is calculated for each of the said mixed samples, and the sum of the respective ratios for the mixed samples is used as a quantification index (see the equation described below).

$$S/Sc(20+50)=(RC-S(20)/RC-Sc(20))\times 100+(RC-S(50)/RC-Sc(50))\times 100$$

In the embodiment, the predetermined threshold value of the quantification index is not particularly limited. The predetermined threshold value can be defined by accumulation of APTT data for healthy people and patients with various diseases who are observed to have prolonged APTTs. Alternatively, the coagulation time is determined for each of a group of normal samples and a group of LA positive samples, thereby to obtain their quantification index values, and based thereon the value at which one group can be clearly distinguished from the other can be set as a predetermined threshold value. Statistical procedures such as ROC analysis can be used to calculate the predetermined threshold value.

The present disclosure is now described the in more detail by way of examples, but is not limited thereto.

EXAMPLES

Example 1

Effects on the sensitivity to LA and to heparin were investigated for APTT reagents with varied concentrations of one of three phospholipids (a PE, a PC and, a PS) contained therein.

(1) Reagents
(1.1) Preparation of liposomes

A solution of the phospholipids in chloroform, containing a given amount of each of dioleoyl (DO) PE (Avanti Polar Lipids, Inc.), DOPC (Avanti Polar Lipids, Inc.), and DOPS (Avanti Polar Lipids, Inc.), was prepared and placed into an eggplant flask. The eggplant flask was rotated on a rotary evaporator to evaporate the chloroform, thereby forming a thin film of the phospholipid on the inner wall of the flask. To the flask was added 1000 mL of buffer (containing TAPS, HEPES, and glycine, pH 7.4) was added to swell the phospholipid thin film, thereby obtaining a buffer containing liposomes. The liposome-containing buffer was stirred by a stirrer at 500 rpm for 60 minutes. Then, the liposome-containing buffer was subjected to sonication at 37 kHz for 15 minutes using a water-bath ultrasonic device UT-306H (Sharp Corporation), thereby allowing the liposomes to disperse in the buffer. The resultant buffer containing the dispersed liposomes was subjected to an extruder treatment using a 0.2 μm polycarbonate membrane (Millipore) and EmulsiFlex-C50 (Avestin), thereby making a liposome-containing buffer in which the particle sizes of the liposomes is homogeneous.

(1.2) Preparation of Activator-Containing Solutions

A solution of ellagic acid was prepared by dissolving 500 mg of ellagic acid (Tokyo Chemical Industry Co., Ltd.) in a 0.1 N aqueous solution of sodium hydroxide. An activator-containing solution was prepared by mixing the resulting ellagic acid solution, 10 mM TAPS buffer (pH 8.6), zinc chloride (Kishida Chemical Co., Ltd.), and aluminum chloride (Kishida Chemical Co., Ltd.).

(1.3) Preparation of APTT Reagents

The liposome-containing buffer thus obtained and the activator-containing solution were mixed to prepare an APTT reagent with a defined phospholipid composition. The composition of the phospholipids in the respective APTT reagents was as shown in Tables 1 to 3. For the APTT reagents in Example 1, the standard concentrations of the PE, the PC, and the PS were 15 µg/mL, 45 µg/mL, and 10 µg/mL, respectively. The components other than the phospholipids in the APTT reagents were: 10 mM TAPS, 50 mM HEPES, 1% (w/w) glycine, 0.1 mM ellagic acid, 60 µM zinc chloride, and 50 µM aluminum chloride. The resulting APTT reagent is also referred to hereinafter as a "first reagent."

TABLE 1

| | Phospholipid varied in concentration PE Deviation from standard concentration (%) | | | | |
|---|---|---|---|---|---|
| | −15 | −10 | 0 | 10 | 15 |
| PE (µg/mL) | 12.75 | 13.5 | 15 | 16.5 | 17.25 |
| PC (µg/mL) | 45 | 45 | 45 | 45 | 45 |
| PS (µg/mL) | 10 | 10 | 10 | 10 | 10 |
| Total phospholipid (µg/mL) | 67.75 | 68.5 | 70 | 71.5 | 72.25 |
| PS/PC ratio | 0.22 | 0.22 | 0.22 | 0.22 | 0.22 |
| PS/PE ratio | 0.78 | 0.74 | 0.67 | 0.61 | 0.58 |

TABLE 2

| | Phospholipid varied in concentration PC Deviation from standard concentration (%) | | | | |
|---|---|---|---|---|---|
| | −15 | −10 | 0 | 10 | 15 |
| PE (µg/mL) | 15 | 15 | 15 | 15 | 15 |
| PC (µg/mL) | 38.25 | 40.5 | 45 | 49.5 | 51.75 |
| PS (µg/mL) | 10 | 10 | 10 | 10 | 10 |
| Total phospholipid (µg/mL) | 63.25 | 65.5 | 70 | 74.5 | 76.75 |
| PS/PC ratio | 0.26 | 0.25 | 0.22 | 0.20 | 0.19 |
| PS/PE ratio | 0.67 | 0.67 | 0.67 | 0.67 | 0.67 |

TABLE 3

| | Phospholipid varied in concentration PS Deviation from standard concentration (%) | | | | |
|---|---|---|---|---|---|
| | −15 | −10 | 0 | 10 | 15 |
| PE (µg/mL) | 15 | 15 | 15 | 15 | 15 |
| PC (µg/mL) | 45 | 45 | 45 | 45 | 45 |
| PS (µg/mL) | 8.5 | 9 | 10 | 11 | 11.5 |
| Total phospholipid (µg/mL) | 68.5 | 69 | 70 | 71 | 71.5 |
| PS/PC ratio | 0.19 | 0.20 | 0.22 | 0.24 | 0.26 |
| PS/PE ratio | 0.57 | 0.60 | 0.67 | 0.73 | 0.77 |

(1.4) Preparation of An Aqueous Solution Containing Calcium Ions

Calcium chloride (Kishida Chemical Co., Ltd.) was dissolved in pure water to prepare a 25 mM aqueous solution of calcium chloride. The resulting aqueous calcium chloride solution is also referred to hereinafter as a "second reagent."

(2) Blood Samples

Coagtrol IX (Sysmex Corporation) was used as a normal sample. LA Positive Control (Precision Bio Logic) was used as an LA-containing sample. Heparin Control (Precision Bio Logic) was used as a heparin-containing sample.

(3) Determination of Coagulation Time

The coagulation time was determined by a fully automated coagulation time analyzer CS-2000i (Sysmex Corporation). A blood sample (50 µl) was warmed at 37° C. for 1 minute. To the warmed blood sample was added the first reagent (50 µl), and the mixture was warmed at 37° C. for 3 minutes. Then, the second reagent (50 µl) was added to the resulting mixture. The change in the amount of light transmitted at a wavelength of 660 nm was measured to determine the coagulation time. As an index of the sensitivity to LA, the LA ratio was calculated from the following formula (I). As an index of the sensitivity to heparin, the heparin ratio was calculated from the following formula (II).

(LA ratio)=(coagulation time of LA-containing sample)/(coagulation time of normal sample)  (I)

(Heparin ratio)=(coagulation time of heparin-containing sample)/(coagulation time of normal sample)  (II)

(4) Results

Figure 3:
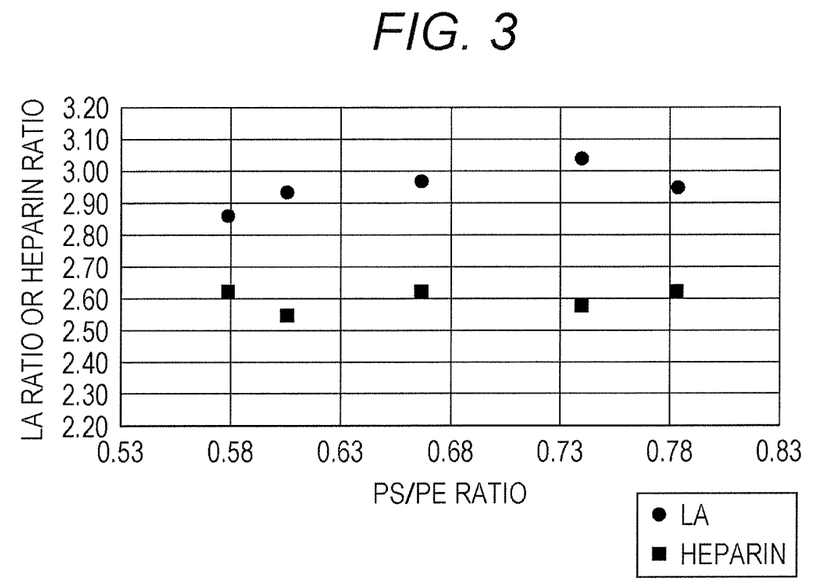
FIG. 3 is a graph plotting LA ratio and heparin ratio against PS/PE ratio in APTT reagents with varied concentrations of PE.
Figure 4:
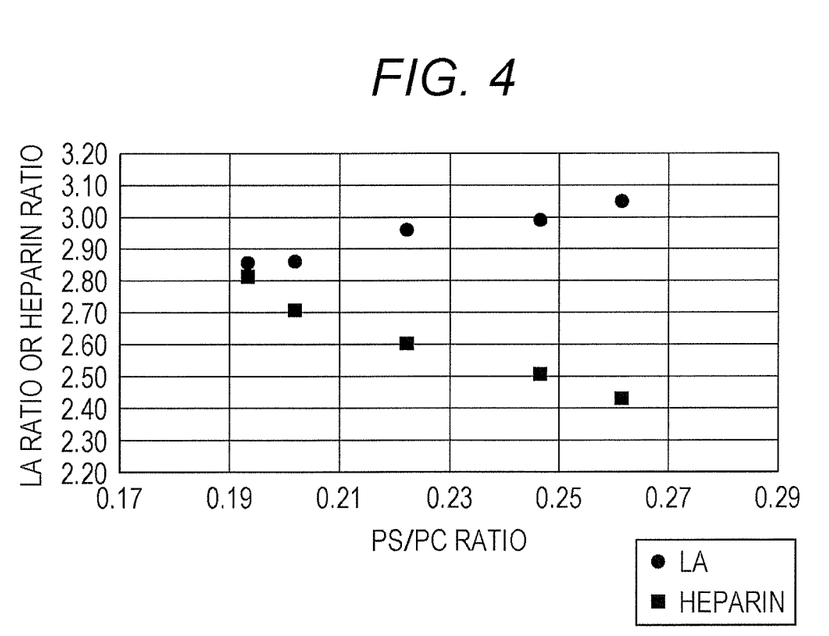
FIG. 4 is a graph plotting LA ratio and heparin ratio against PS/PC ratio in APTT reagents with varied concentrations of PC.
Figure 5:
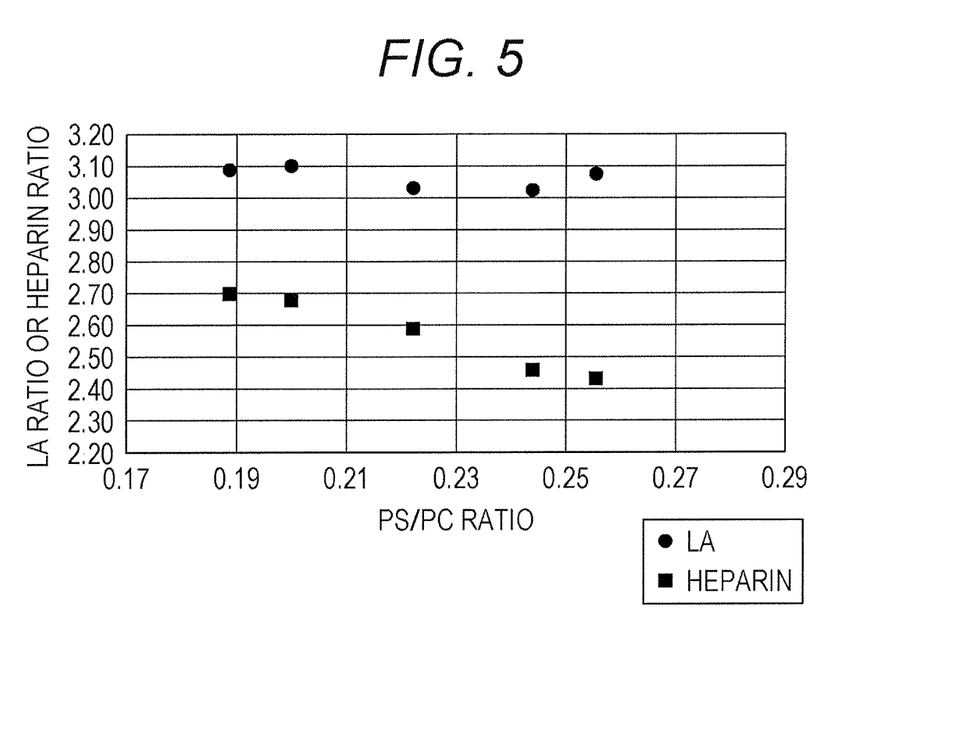
FIG. 5 is a graph plotting LA ratio and heparin ratio against PS/PC ratio in APTT reagents with varied concentrations of PS.

The coagulation times of the respective blood samples, the LA ratios and the heparin ratios are shown in Tables 4 to 6. The LA ratios and the heparin ratios are plotted against the PS/PE ratios in the APTT reagents with varied PE concentrations. Similarly, the LA ratios and the heparin ratios are plotted against the PS/PC ratios in the APTT reagents with varied PC concentrations and with varied PS concentrations. The results are shown in FIGS. 3 to 5.

TABLE 4

| | Phospholipid varied in concentration PE Deviation from standard concentration (%) | | | | |
|---|---|---|---|---|---|
| | −15 | −10 | 0 | 10 | 15 |
| Normal sample (sec.) | 27.9 | 27.6 | 27.6 | 27.8 | 28.1 |
| LA containing sample (sec.) | 82.2 | 83.8 | 81.9 | 81.5 | 80.3 |
| Heparin containing sample (sec.) | 72.9 | 71.0 | 72.1 | 70.7 | 73.3 |
| LA ratio | 2.95 | 3.04 | 2.97 | 2.93 | 2.86 |
| Heparin ratio | 2.61 | 2.57 | 2.61 | 2.54 | 2.61 |

TABLE 5

| | Phospholipid varied in concentration PC Deviation from standard concentration (%) | | | | |
|---|---|---|---|---|---|
| | −15 | −10 | 0 | 10 | 15 |
| Normal sample (sec.) | 26.3 | 26.8 | 26.9 | 27.8 | 28.1 |
| LA containing sample (sec.) | 80.1 | 80.1 | 79.6 | 79.5 | 80.2 |
| Heparin containing sample (sec.) | 63.8 | 67.2 | 69.9 | 75.2 | 78.8 |
| LA ratio | 3.05 | 2.99 | 2.96 | 2.86 | 2.85 |
| Heparin ratio | 2.43 | 2.51 | 2.60 | 2.71 | 2.80 |

TABLE 6

| | Phospholipid varied in concentration PS Deviation from standard concentration (%) | | | | |
|---|---|---|---|---|---|
| | −15 | −10 | 0 | 10 | 15 |
| Normal sample (sec.) | 28.5 | 28.2 | 27.5 | 26.9 | 26.8 |
| LA containing sample (sec.) | 88.0 | 87.5 | 83.3 | 81.3 | 82.4 |
| Heparin containing sample (sec.) | 76.7 | 75.3 | 70.8 | 66.0 | 65.0 |
| LA ratio | 3.09 | 3.10 | 3.03 | 3.02 | 3.07 |
| Heparin ratio | 2.69 | 2.67 | 2.57 | 2.45 | 2.43 |

In the field of blood testing, APTT reagents are generally required to allow the coagulation time to be about 30 seconds for normal samples. As can be seen from Tables 4 to 6, the normal sample had a coagulation time of about 30 seconds, regardless of which APTT reagent was used. As can be seen from FIGS. 3 to 5, a correlation was suggested between the PS/PC ratios and the LA ratio of the APTT reagents with varied PC concentrations. That is, it was revealed that the sensitivity to LA was improved with increasing PS/PC ratios of the APTT reagents with varied PC concentrations.

Example 2

Effects on the sensitivity to LA and to heparin were further investigated for APTT reagents with a fixed PS concentration and varied PC concentrations. For comparison, commercially available APTT reagents were also used.
(1) Reagents
(1.1) First and Second Reagents
The phospholipids employed DOPE, DOPC, and DOPS. APTT reagents with varied PC concentrations were prepared as in Example 1. For the APTT reagents in Example 2, the standard concentrations of the PE, the PC, and the PS were 15 μg/mL, 45 μg/mL, and 10 μg/mL, respectively. The composition of the phospholipids in the respective APTT reagents was as shown in Table 7. The second reagent in Example 1 was used as an aqueous solution containing calcium ions.

TABLE 7

| | Phospholipid varied in concentration PC Deviation from standard concentration (%) | | | | | | |
|---|---|---|---|---|---|---|---|
| | −33.3 | −15 | −10 | 0 | 10 | 15 | 33.3 |
| PE (μg/mL) | 15 | 15 | 15 | 15 | 15 | 15 | 15 |
| PC (μg/mL) | 30 | 38.25 | 40.5 | 45 | 49.5 | 51.75 | 60 |
| PS (μg/mL) | 10 | 10 | 10 | 10 | 10 | 10 | 10 |

TABLE 7-continued

| | Phospholipid varied in concentration PC Deviation from standard concentration (%) | | | | | | |
|---|---|---|---|---|---|---|---|
| | −33.3 | −15 | −10 | 0 | 10 | 15 | 33.3 |
| Total phospholipid (μg/L) | 55 | 63.25 | 65.5 | 70 | 74.5 | 76.75 | 85 |
| PS/PC | 0.33 | 0.26 | 0.25 | 0.22 | 0.2 | 0.19 | 0.17 |

Figure 6:
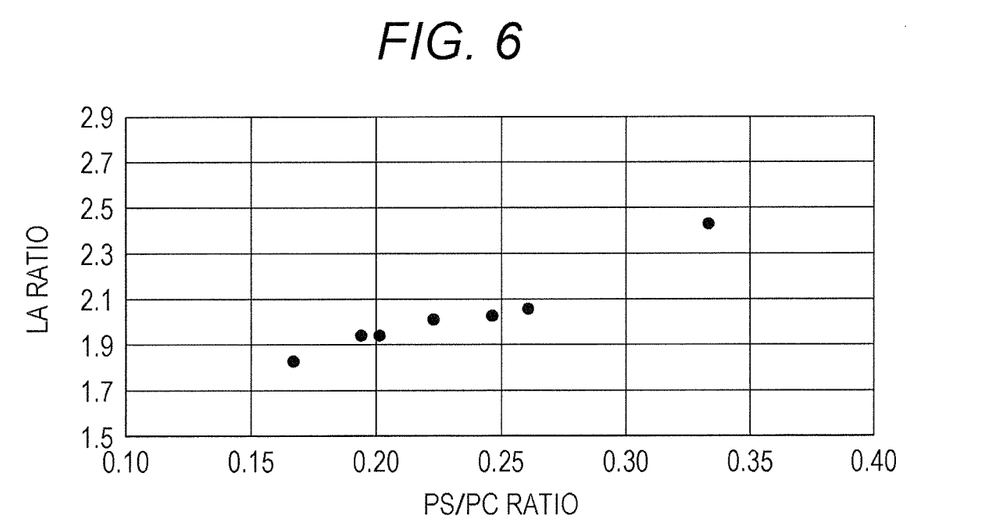
FIG. 6 is a graph plotting LA ratio against PS/PC ratio in APTT reagents with varied concentrations of PC.
Figure 7:
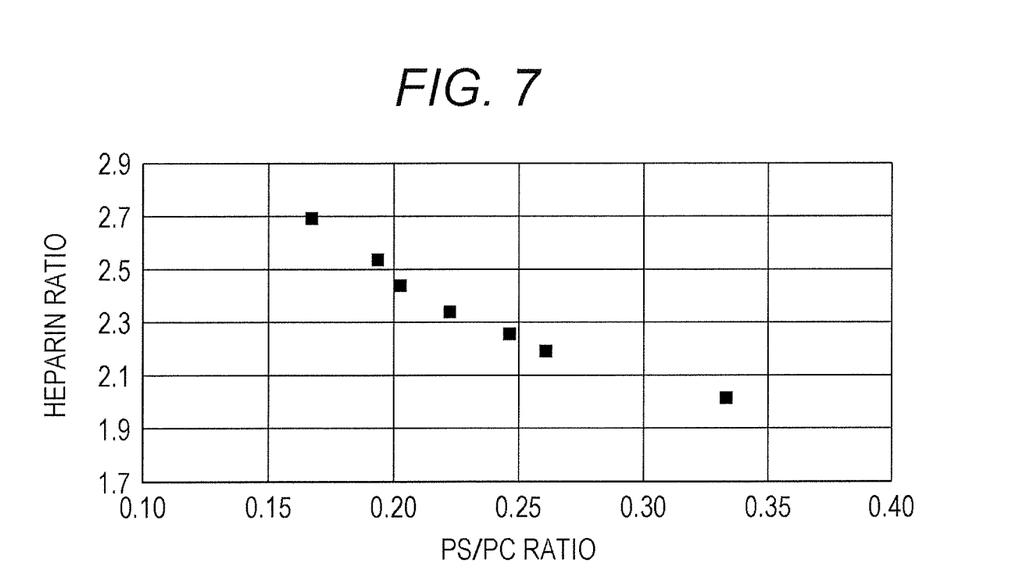
FIG. 7 is a graph plotting heparin ratio against PS/PC ratio in APTT reagents with varied concentration of PC.

(1.2) Commercial Available APTT Reagents
Four commercially available APTT reagents were used for comparison with APTT reagents according to the embodiment. The four commercially available reagents are also referred to hereinafter as Products A to D, respectively. Product A is Thrombocheck APTT-SLA (Sysmex Corporation). Product B is Coagpia® APTT-S (Sekisui Medical Co., Ltd.). Product C is Actin FS (Sysmex Corporation). Product D is HemosIL SynthASil APTT (I.L. Japan Co., Ltd.). Product A is known as an APTT reagent with moderate sensitivity to LA and to heparin. Product B is known as an APTT reagent with high sensitivity to LA. Product C is known as an APTT reagent with moderate sensitivity to heparin. Product D is known as an APTT reagent with high sensitivity to heparin. Product C is known to have little sensitivity to LA.
(2) Blood Samples
Weak LA Positive Control (Precision Bio Logic) was used as a LA-containing sample. This sample has an LA content lower than that of the LA-containing sample used in Example 1. The normal sample and the heparin-containing sample were the same as in Example 1.
(3) Determination of Coagulation Time
The coagulation times of the respective blood samples were determined using the first and second reagents in a similar way as in Example 1. The LA ratios and the heparin ratios were calculated based on the coagulation times obtained. The coagulation times of the respective blood samples were also determined using the above-mentioned commercially available reagents, thereby calculating the LA ratios and the heparin ratios. Regardless of which APTT reagent was used, the coagulation time was determined by a fully automated coagulation time analyzer CS-2000i (Sysmex Corporation).
(4) Results
For each of the APTT reagents, the phospholipid composition, the PS/PC ratio, the coagulation time of the normal sample, the LA ratio, and the heparin ratio are shown in Table 8. In the table, APTT reagents A to D refer to Products A to D, respectively. The LA ratios and the heparin ratios are plotted against the PS/PC ratios in the APTT reagents prepared in Example 2. The results are shown in FIGS. 6 and 7. As can be seen from Table 8, the normal sample had a coagulation time of about 30 seconds, regardless of which APTT reagent was used.

TABLE 8

| | APTT reagent | | | | | | | | | | |
|---|---|---|---|---|---|---|---|---|---|---|---|
| | Reagent according the present invention | | | | | | | A | B | C | D |
| PE (μg/mL) | 15 | 15 | 15 | 15 | 15 | 15 | 15 | 30 | | | |
| PC (μg/mL) | 30 | 38.25 | 40.5 | 45 | 49.5 | 51.75 | 60 | 56 | | | |
| PS (μg/mL) | 10 | 10 | 10 | 10 | 10 | 10 | 10 | 19 | | | |
| PS/PC ratio | 0.33 | 0.26 | 0.25 | 0.22 | 0.20 | 0.19 | 0.17 | 0.34 | | | |
| Coagulation time of normal sample (sec.) | 26.9 | 26.3 | 26.8 | 26.9 | 27.8 | 28.1 | 30.4 | 27.7 | | | |

TABLE 8-continued

| | APTT reagent | | | | | | | | | |
|---|---|---|---|---|---|---|---|---|---|---|
| | Reagent according the present invention | | | | | | | A | B | C | D |
| LA ratio | 2.43 | 2.05 | 2.02 | 2.00 | 1.93 | 1.93 | 1.83 | 1.54 | 1.77 | | |
| Heparin ratio | 2.01 | 2.18 | 2.25 | 2.33 | 2.43 | 2.52 | 2.69 | 1.87 | | 2.19 | 2.86 |

As shown in Table 8, any of the APTT reagents according to the embodiment exhibited a higher LA ratio and a higher heparin ratio than Product A did. Any one of the APTT reagents according to the embodiment exhibited a higher LA ratio than Product B did, which exhibits high sensitivity to LA. Therefore, it was suggested that the sensitivity to LA could be improved by APTT reagents having a PS/PC ratio of not less than 0.17.

In Example 2, the composition of the phospholipids making the heparin ratio appropriate was examined using, as an index, the heparin ratio when Products C and D having different sensitivities to heparin were used. Specifically, examinations were made to determine the range of PS/PC ratios allowing the heparin ratio to be not less than 2.19 and not more than 2.86. Table 8 suggested that APTT reagents having a PS/PC ratio of not less than 0.17 and not more than 0.25 would make the sensitivity to heparin more appropriate.

Example 3

Effects on the sensitivity to LA and to heparin were investigated for APTT reagents with a fixed concentration ratio PS/PC and varied concentrations of each of the phospholipids.
(1) Reagents and Blood Samples
The phospholipids employed DOPE, DOPC, and DOPS. APTT reagents in which the concentrations of the respective phospholipids were varied with a fixed PS/PC ratio of 0.22 were prepared as in Example 1. The composition of the phospholipids in the respective APTT reagents was as shown in Table 9. The second reagent in Example 1 was used as an aqueous solution containing calcium ions. The normal sample, the LA-containing sample, and the heparin-containing sample were the same as in Example 2.

TABLE 9

| PE (µg/mL) | 24 | 21 | 18 | 15 | 12 | 9 | 6 |
|---|---|---|---|---|---|---|---|
| PC (µg/mL) | 72 | 63 | 54 | 45 | 36 | 27 | 18 |
| PS (µg/mL) | 16 | 14 | 12 | 10 | 8 | 6 | 4 |
| Total phospholipid (µg/mL) | 112 | 98 | 84 | 70 | 56 | 42 | 28 |
| PS/PC ratio | 0.22 | 0.22 | 0.22 | 0.22 | 0.22 | 0.22 | 0.22 |

Figure 8:
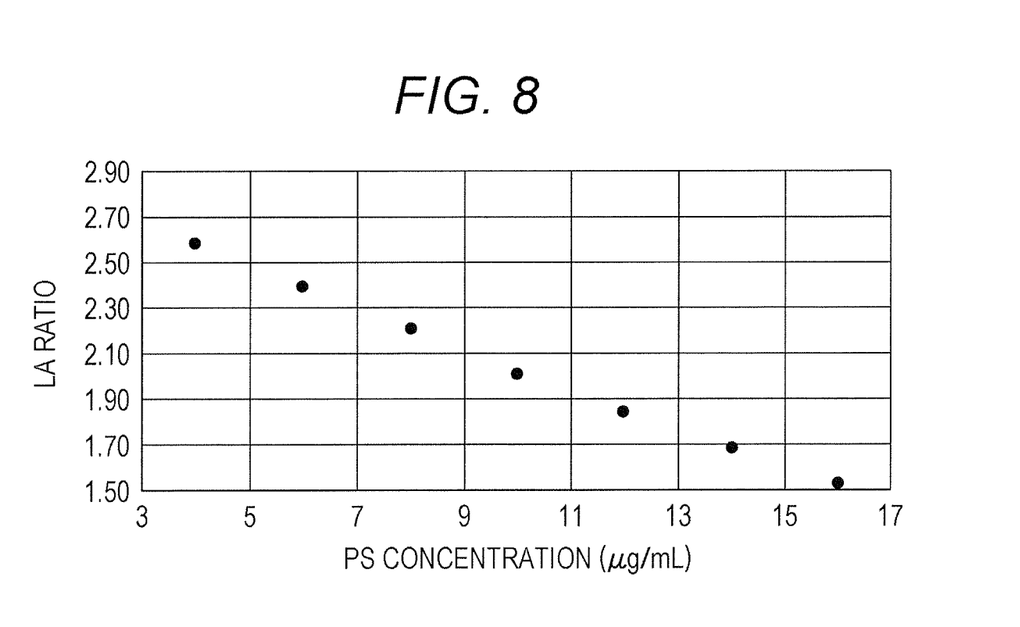
FIG. 8 is a graph plotting LA ratio against the concentration of PS in APTT reagents with a fixed PS/PC ratio.
Figure 9:
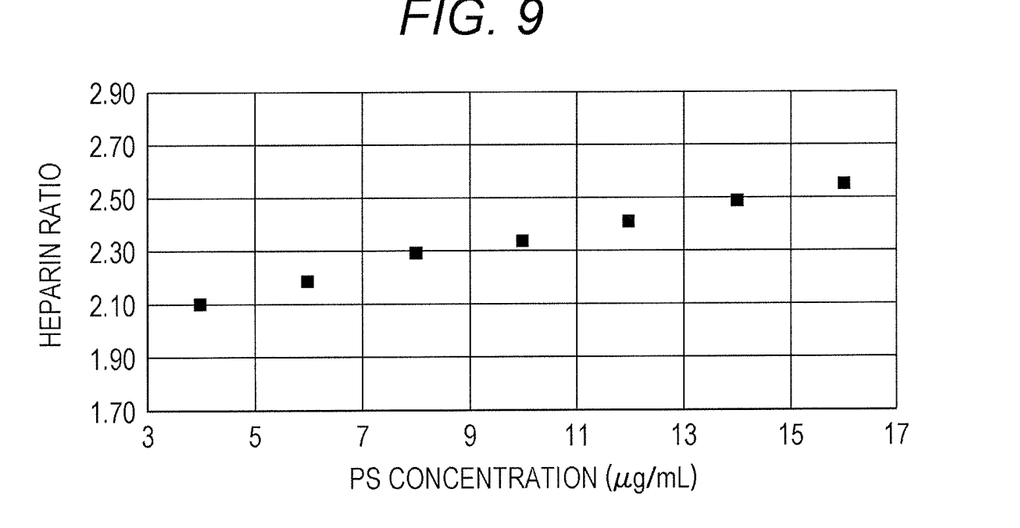
FIG. 9 is a graph plotting heparin ratio against the concentration of PS in APTT reagents with a fixed PS/PC ratio.

(2) Determination of Coagulation Time
The coagulation times of the respective blood samples were determined using the first and second reagents in a similar way as in Example 1. The LA ratios and the heparin ratios were calculated based on the coagulation times obtained.
(3) Results
For each of the APTT reagents, the phospholipid composition, the PS/PC ratio, the coagulation time of the normal sample, the LA ratio, and the heparin ratio are shown in Table 10. The LA ratios and the heparin ratios are plotted against the PS concentrations in the APTT reagents prepared in Example 3. The results are shown in FIGS. 8 and 9. As can be seen from Table 10, the normal sample had a coagulation time of about 30 seconds, regardless of which APTT reagent was used.

TABLE 10

| PE (µg/mL) | 24 | 21 | 18 | 15 | 12 | 9 | 6 |
|---|---|---|---|---|---|---|---|
| PC (µg/mL) | 72 | 63 | 54 | 45 | 36 | 27 | 18 |
| PS (µg/mL) | 16 | 14 | 12 | 10 | 8 | 6 | 4 |
| PS/PC ratio | 0.22 | 0.22 | 0.22 | 0.22 | 0.22 | 0.22 | 0.22 |
| Coagulation time of normal sample (sec.) | 27.1 | 26.9 | 26.9 | 26.9 | 26.8 | 27.3 | 28.3 |
| LA ratio | 1.52 | 1.68 | 1.83 | 2.00 | 2.20 | 2.39 | 2.58 |
| Heparin ratio | 2.54 | 2.48 | 2.41 | 2.33 | 2.29 | 2.18 | 2.10 |

The LA ratio of Product B used in Example 2 was used as an index of the sensitivity to LA to examine the range of suitable concentrations of the PS in the APTT reagent. Accordingly, examinations were made to determine the range of PS concentrations allowing the LA ratio to be not less than 1.77. It was suggested from Table 10 and FIGS. 8 and 9 that the sensitivity to LA is improved by APTT reagents having a PS concentration of not less than 4 µg/mL and not more than 13 µg/mL. The heparin ratios of Products C and D were used as an index of the sensitivity to heparin to examine the range of suitable concentrations of the PS in the APTT reagent. Accordingly, examinations were made to determine the range of PS concentrations allowing the heparin ratio to be not less than 2.19 and not more than 2.86. It was suggested from Table 10 and FIGS. 8 and 9 that APTT reagents having a PS concentration of not less than 7 µg/mL have an appropriate sensitivity to heparin. These examination results suggested that APTT reagents having a PS concentration of not less than 7 µg/mL and not more than 13 µg/mL have an improved sensitivity to LA and an appropriate sensitivity to heparin.

Reference Example 1

Effects on the sensitivity to LA were investigated for APTT reagents with a fixed composition of the phospholipids and varied concentrations of ellagic acid.
(1) Reagents and Blood Samples
The phospholipids employed DOPE, DOPC, and DOPS. APTT reagents with different concentrations of ellagic acid were prepared as in Example 1. The concentration of ellagic acid in each of the APTT reagents was 32, 48, 64, 80, 96, 112, or 128 µM. The APTT reagents all had concentrations of the PE, the PC, and the PS of 15 µg/mL, 45 µg/mL, and 10 µg/mL, respectively, and a PS/PC ratio of 0.22. The second reagent in Example 1 was used as an aqueous solution containing calcium ions. The normal sample and the LA-containing sample were the same as in Example 1.
(2) Determination of Coagulation Time
The coagulation times of the respective blood samples were determined using the first and second reagents in a similar way as in Example 1. The LA ratio was calculated based on the coagulation times obtained.

(3) Results

Figure 10:
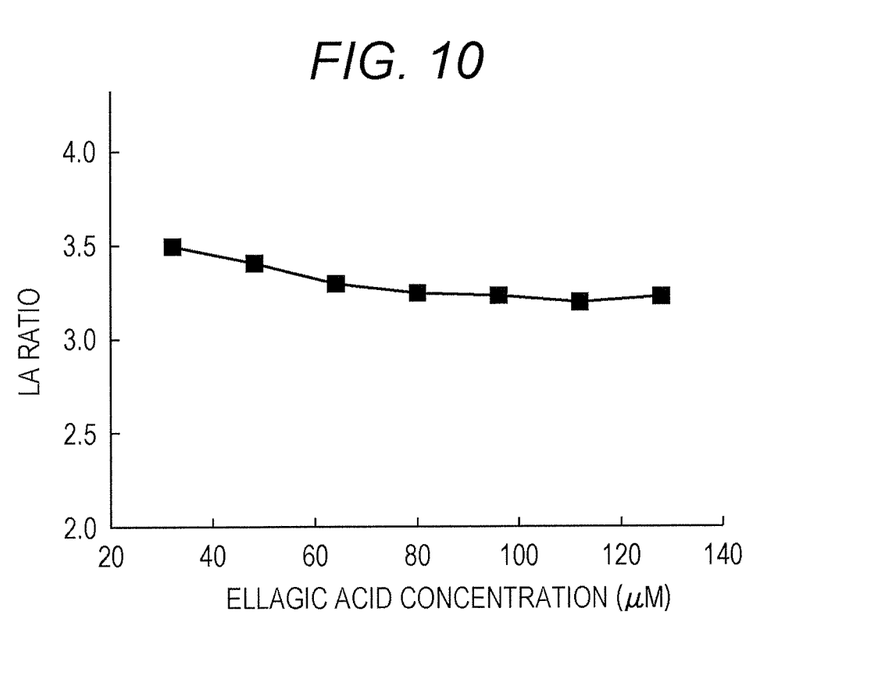
FIG. 10 is a graph plotting LA ratio against the concentration of ellagic acid in APTT reagents with a fixed phospholipid composition.

For each of the APTT reagents, the concentration of ellagic acid, the coagulation time of the normal sample, and the LA ratio are shown in Table 11. The LA ratios are plotted against the concentrations of ellagic acid in the APTT reagents prepared in Reference Example 1. The results are shown in FIG. 10. As can be seen from Table 11, the normal sample had a coagulation time of about 30 seconds, regardless of which APTT reagent was used.

TABLE 11

| | Ellagic acid (µM) | | | | | | |
|---|---|---|---|---|---|---|---|
| | 32 | 48 | 64 | 80 | 96 | 112 | 128 |
| Coagulation time of normal sample (sec.) | 28.1 | 27.2 | 26.7 | 26.5 | 26.8 | 27.6 | 29.0 |
| LA ratio | 3.50 | 3.40 | 3.29 | 3.25 | 3.24 | 3.20 | 3.22 |

As can be seen from Table 11 and FIG. 10, the concentration of ellagic acid in the APTT reagent was found to have little effect on the sensitivity to LA.

Example 4

Effects on the sensitivity to LA and to heparin were investigated for APTT reagents with a concentration ratio PS/PC lower than that of an APTT reagent with standard concentrations of the phospholipids.

(1) Reagents and Blood Samples

The phospholipids employed DOPE, DOPC, and DOPS. APTT reagents with a concentration ratio PS/PC lower than that of an APTT reagent with standard concentrations of the phospholipids were prepared as in Example 1. For the APTT reagents in Example 4, the standard concentrations of the PE, the PC, and the PS were 15 µg/mL, 45 µg/mL, and 10 µg/mL, respectively. The composition of the phospholipids in the respective APTT reagents was as shown in Table 12. In the table, APTT reagent 1 was an APTT reagent with the standard concentrations of the phospholipids. APTT reagents 2 and 3 had a PS/PC ratio lower than that of APTT reagent 1 by decreasing the concentration of the PS in the reagent. APTT reagents 4 and 5 had a PS/PC ratio lower than that of APTT reagent 1 by increasing the concentration of the PC in the reagent. For comparison, Products A and D used in Example 2 were also used in Example 4. The second reagent in Example 1 was used as an aqueous solution containing calcium ions. The normal sample, the LA-containing sample, and the heparin-containing sample were the same as in Example 2.

TABLE 12

| | APTT reagent | | | | |
|---|---|---|---|---|---|
| | 1 | 2 | 3 | 4 | 5 |
| PE (µg/mL) | 15 | 15 | 15 | 15 | 15 |
| PC (µg/mL) | 45 | 45 | 45 | 70 | 90 |
| PS (µg/mL) | 10 | 7 | 5 | 10 | 10 |
| Total phospholipid (µg/L) | 70 | 67 | 65 | 95 | 115 |
| PS/PC ratio | 0.22 | 0.16 | 0.11 | 0.14 | 0.11 |

(2) Determination of Coagulation Time

The coagulation times of the respective blood samples were determined using the first and second reagents in a similar way as in Example 1. The LA ratios and the heparin ratios were calculated based on the coagulation times obtained.

(3) Results

For each of the APTT reagents, the phospholipid composition, the PS/PC ratio, the coagulation times of the respective samples, the LA ratio, and the heparin ratio are shown in Table 13. As can be seen from Table 13, the normal sample had a coagulation time of about 30 seconds, regardless of which APTT reagent was used.

TABLE 13

| | APTT reagent | | | | | | |
|---|---|---|---|---|---|---|---|
| | 1 | 2 | 3 | 4 | 5 | A | D |
| PE (µg/mL) | 15 | 15 | 15 | 15 | 15 | 30 | |
| PC (µg/mL) | 45 | 45 | 45 | 70 | 90 | 56 | |
| PS (µg/mL) | 10 | 7 | 5 | 10 | 10 | 19 | |
| PS/PC | 0.22 | 0.16 | 0.11 | 0.14 | 0.11 | 0.34 | |
| Normal sample (sec.) | 25.8 | 29.4 | 32 | 30.4 | 32.7 | 27.8 | |
| LA containing sample (sec.) | 65.7 | 89.2 | 95.4 | 78.3 | 74.5 | 47.0 | |
| Heparin containing sample (sec.) | 56.6 | 79.8 | 94.5 | 93.6 | 120.2 | 51.6 | |
| LA ratio | 2.55 | 3.03 | 2.98 | 2.58 | 2.28 | 1.69 | |
| Heparin ratio | 2.19 | 2.71 | 2.95 | 3.08 | 3.68 | 1.86 | 2.86 |

In Example 4, the LA ratio of Product B used in Example 2 (1.77) was used as an index of the sensitivity to LA for the APTT reagents. As shown in Table 13, any one of the APTT reagents 1 to 5 exhibited a LA ratio of not less than 1.77. In Example 4, the heparin ratios of Products C and D used in Example 2 were used as an index of the sensitivity to heparin for the APTT reagents. Accordingly, examinations were made to determine the range of PS/PC ratios allowing the heparin ratio to be not less than 2.19 and not more than 2.86. As shown in Table 13, APTT reagents 1 and 2 exhibited a heparin ratio of not less than 2.19 and not more than 2.86. Therefore, it was suggested that APTT reagents having a PS/PC ratio of not less than 0.16 have an improved sensitivity to LA and an appropriate sensitivity to heparin.

As shown in Table 13, APTT reagents with a PS/PC ratio of lower than 0.16 tended to result in an excessive increase in the sensitivity to heparin. Heparin is a substance that is negatively charged, and the PS is a phospholipid that is negatively charged. Thus, as the proportion of the PS on the surface of a liposome decreases, the negative charge on the surface thereof decreases and the heparin becomes more likely to interact with the liposome. Therefore, it is considered that the APTT reagents with a decreased PS/PC ratio have an increased sensitivity to heparin. However, APTT reagents that are excessively sensitive to heparin are not suitable for monitoring of heparin therapy. The results from Examples 2 and 4 suggested that APTT reagents having a PS/PC ratio of not less than 0.16 and not more than 0.25 improves the sensitivity to LA and have an appropriate sensitivity to heparin, of the APTT reagent.

Reference Example 2

Effects on the sensitivity to LA and to heparin were investigated for APTT reagents having a fixed concentration ratio PS/PC and concentrations of each of the phospholipids decreased below their standard concentrations.

(1) Reagents and Blood Samples

The phospholipids employed DOPE, DOPC, and DOPS. APTT reagents in which the concentrations of the respective phospholipids were decreased below their standard concentrations, with a fixed PS/PC ratio of 0.22 were prepared as in Example 1. For the APTT reagents in Reference Example 2, the standard concentrations of the PE, the PC, and the PS were 15 μg/mL, 45 μg/mL, and 10 μg/mL, respectively. The composition of the phospholipids in the respective APTT reagents was as shown in Table 14. In the table, APTT reagent 1 was an APTT reagent with the standard concentrations of the phospholipids. In APTT reagent 2, the concentration of each of the phospholipids was half relative to that in APTT reagent 1. In APTT reagent 3, the concentration of each of the phospholipids was one-fourth relative to that in APTT reagent 1. The second reagent in Example 1 was used as an aqueous solution containing calcium ions. The normal sample, the LA-containing sample, and the heparin-containing sample were the same as in Example 2.

TABLE 14

|  | APTT reagent | | |
| --- | --- | --- | --- |
|  | 1 | 2 | 3 |
| PE (μg/mL) | 15 | 7.5 | 3.75 |
| PC (μg/mL) | 45 | 22.5 | 11.25 |
| PS (μg/mL) | 10 | 5 | 2.5 |
| Total phospholipid (μg/L) | 70 | 35 | 17.5 |
| PS/PC ratio | 0.22 | 0.22 | 0.22 |

(2) Determination of Coagulation Time

The coagulation times of the respective blood samples were determined using the first and second reagents in a similar way as in Example 1. The LA ratios and the heparin ratios were calculated based on the coagulation times obtained.

(3) Results

For each of the APTT reagents, the phospholipid composition, the PS/PC ratio, the coagulation time of the normal sample, the LA ratio, and the heparin ratio are shown in Table 15. As can be seen from Table 15, the normal sample had a coagulation time of about 30 seconds, regardless of which APTT reagent was used.

TABLE 15

|  | APTT reagent | | |
| --- | --- | --- | --- |
|  | 1 | 2 | 3 |
| PE (μg/mL) | 15 | 7.5 | 3.75 |
| PC (μg/mL) | 45 | 22.5 | 11.25 |
| PS (μg/mL) | 10 | 5 | 2.5 |
| PS/PC | 0.22 | 0.22 | 0.22 |
| Normal sample (sec.) | 25.8 | 27.1 | 29.7 |
| LA containing sample (sec.) | 65.7 | 90.9 | 113.5 |
| Heparin containing sample (sec.) | 56.6 | 56.9 | 59.9 |
| LA ratio | 2.55 | 3.35 | 3.82 |
| Heparin ratio | 2.19 | 2.10 | 2.02 |

In Reference Example 2, the heparin ratios of Products C and D used in Example 2 were used as an index of the sensitivity to heparin for the APTT reagents. Accordingly, examinations were made to determine the range of PS concentrations allowing the heparin ratio to be not less than 2.19 and not more than 2.86. As shown in Table 15, APTT reagent 1 had a heparin ratio of 2.19, whereas APTT reagents 2 and 3 had a heparin ratio below 2.19. Thus, it was demonstrated that lower concentrations of the PS in APTT reagents resulted in a decrease in the sensitivity to heparin. The results from Reference Example 2 are consistent with the results from Example 3.

The invention claimed is:

1. A method for determination of activated partial thromboplastin time, comprising:
   mixing a blood sample, a first reagent containing a phosphatidylcholine (PC), a phosphatidylserine (PS), and a phosphatidylethanolamine (PE), and a second reagent containing calcium ions; and
   measuring a coagulation time of the blood sample, wherein
   a concentration ratio of the PS relative to the PC in the first reagent is not less than 0.16 and not more than 0.25,
   a concentration of the PS in the first reagent is not less than 7 μg/mL and not more than 13 μg/mL, and
   a concentration of the PE in the first reagent is more than 9 μg/mL and less than 25 μg/mL.

2. The method according to claim 1, wherein the first reagent and the blood sample are mixed at a mixing ratio of 8:2 to 2:8 by volume.

3. The method according to claim 1, further comprising determining a presence or absence of lupus anticoagulant in the blood sample, when the blood sample is observed to have a coagulation time longer than that of a normal sample.

4. The method according to claim 3, wherein the coagulation time observed in the blood sample is determined by measuring a coagulation time of a normal sample using the first reagent and the second reagent, and based on a result of comparison between the coagulation times of the blood sample and of the normal sample.

5. The method according to claim 3, wherein the presence or absence of lupus anticoagulant is determined by measuring a coagulation time of a mixed sample of the blood sample and the normal sample using the first reagent and the second reagent, and based on the coagulation times of the mixed sample, of the blood sample, and of the normal sample.

6. The method according to claim 1, wherein the mixture of the blood sample, the first reagent, and the second reagent is irradiated with light, to obtain optical information on transmittance and the coagulation time is determined based on the optical information.

* * * * *